(12) United States Patent
Trumble et al.

(10) Patent No.: US 7,540,874 B2
(45) Date of Patent: Jun. 2, 2009

(54) METHOD AND DEVICE FOR USE IN OSTEOTOMY

(75) Inventors: Thomas E Trumble, Mercer Island, WA (US); Lars Tellman, Falsterbo (SE)

(73) Assignee: TriMed Inc., Valencia, CA (US)

( * ) Notice: Subject to any disclaimer, the term of this patent is extended or adjusted under 35 U.S.C. 154(b) by 11 days.

(21) Appl. No.: 10/854,892

(22) Filed: May 27, 2004

(65) Prior Publication Data

US 2005/0277941 A1    Dec. 15, 2005

(51) Int. Cl.
*A61B 17/00*    (2006.01)
(52) U.S. Cl. ................... 606/79; 606/105; 606/86 B; 606/282
(58) Field of Classification Search ............... 606/87, 606/96, 79, 105, 86 B, 89, 70, 71, 280–299, 606/53, 915
See application file for complete search history.

(56) References Cited

U.S. PATENT DOCUMENTS 1,789,060 A * 1/1931 Weisenbach ............ 606/54
3,244,170 A * 4/1966 McElvenny ............ 606/71

(Continued)

FOREIGN PATENT DOCUMENTS

FR    2705881 A    12/1994

(Continued)

OTHER PUBLICATIONS

Rayhack J.M., Gasser S.I., Latta L.L., Ouellette E.A., Milne E.L., "Precision oblique osteotomy for shortening of the ulna", J Hand Surg [Am]. Sep. 1993;18(5):908 (from Medline).

*Primary Examiner*—Alvin J Stewart
(74) *Attorney, Agent, or Firm*—Finnegan, Henderson, Farabow, Garrett & Dunner, L.L.P.

(57) ABSTRACT

Method and device to be used in osteotomy in securing two separated parts of a bone in relation to each other before and after removing an excessive part thereof. After removing and/or holding/keeping apart tissue like muscles, tendons, skin and so on, a longitudinally shaped fixation device is applied atop of a site of said bone (B) where the excision is to be performed. The device is secured with the use of one or more nails or screws at one first end thereof with the use of a hole or holes providing a snug fit to the bone as well as the device. The fixation device is secured at its other second end with the use of one or more elongated holes or slots in the longitudinal direction of the fixation device, which holes once the bone portion to be excised is taken away, provide for movability of the bone ends thus created towards each other. This is temporarily achieved by using prefabricated gliding pins and guiding holes in the respective parts fixing a cutting guide to the fixation device enabling a controlled cutting of a part of bone to be excised. After cutting the bone to a preferred configuration the bone ends created are pushed towards and into contact with each other whereafter a screw is driven into a prefabricated hole in the fixation device to transversely penetrate and snugly fit the taxation device and both bone ends together, keeping a steady state, during which at least one screw is snugly fitted to the other second end of the bone such as to finally keep the bone ends together in order to heal.

6 Claims, 17 Drawing Sheets

U.S. PATENT DOCUMENTS

| | | | |
|---|---|---|---|
| 3,386,437 A * | 6/1968 | Treace | 606/105 |
| 3,400,711 A * | 9/1968 | Frick et al. | 606/105 |
| 4,119,092 A * | 10/1978 | Gil | 606/96 |
| 4,187,841 A * | 2/1980 | Knutson | 606/105 |
| 4,570,625 A * | 2/1986 | Harris et al. | 606/58 |
| 4,929,247 A | 5/1990 | Rayhack | |
| 5,042,983 A | 8/1991 | Rayhack | |
| 5,129,903 A * | 7/1992 | Luhr et al. | 606/71 |
| 5,167,665 A * | 12/1992 | McKinney | 606/75 |
| 5,176,685 A * | 1/1993 | Rayhack | 606/87 |
| 5,234,434 A * | 8/1993 | Goble et al. | 606/96 |
| 5,275,599 A * | 1/1994 | Zbikowski et al. | 606/54 |
| 5,352,228 A * | 10/1994 | Kummer et al. | 606/64 |
| 5,662,649 A * | 9/1997 | Huebner | 606/57 |
| 5,749,873 A * | 5/1998 | Fairley | 606/70 |
| 5,902,304 A * | 5/1999 | Walker et al. | 606/71 |
| 5,951,557 A * | 9/1999 | Luter | 606/286 |
| 5,964,763 A * | 10/1999 | Incavo et al. | 606/71 |
| 5,973,223 A * | 10/1999 | Tellman et al. | 606/65 |
| 5,976,138 A * | 11/1999 | Baumgart et al. | 606/62 |
| 6,007,535 A | 12/1999 | Rayhack et al. | |
| 6,027,504 A * | 2/2000 | McGuire | 606/87 |
| 6,066,142 A * | 5/2000 | Serbousek et al. | 606/96 |
| 6,183,475 B1 * | 2/2001 | Lester et al. | 606/281 |
| 6,678,562 B1 * | 1/2004 | Tepper et al. | 607/51 |
| 7,182,766 B1 * | 2/2007 | Mogul | 606/87 |
| 7,189,237 B2 * | 3/2007 | Huebner | 606/291 |
| 7,326,212 B2 * | 2/2008 | Huebner | 606/328 |
| 7,425,213 B2 * | 9/2008 | Orbay | 606/62 |
| 2002/0143335 A1 * | 10/2002 | von Hoffmann et al. | 606/67 |
| 2005/0090900 A1 * | 4/2005 | Nordquist | 623/17.11 |
| 2006/0200134 A1 * | 9/2006 | Freid et al. | 606/61 |
| 2007/0270850 A1 * | 11/2007 | Geissler | 606/69 |
| 2008/0275451 A1 * | 11/2008 | McAllister et al. | 606/87 |

FOREIGN PATENT DOCUMENTS

RU 2183435 C 6/2002

* cited by examiner

METHOD AND DEVICE FOR USE IN OSTEOTOMY

FIELD OF INVENTION

The present invention relates generally to a method and a device adapted for use in connection with a surgical osteotomy, and more specifically a device for use during a bone-shortening operation for the treatment or correction of deformity related to excessive bone length.

BACKGROUND AND PRIOR ART

It is known to the art the difficulties to treat a bone fracture near a joint. Prior known methods and arrangements in this context have not safeguarded all necessary requirements when it comes to accuracy in fixation of bone parts using methods including a cutting sequence. In unfortunate circumstances a poor accuracy may later on affect the healing process as well as the rigidity of the bone parts when a normal healing period or process has passed, with possible further convalescence or re-operation required.

The present invention is described in connection with fracture disorders related to the wrist, particularly those that result in misalignment between a first part of a bone named radius, and another part of a bone named ulna, causing interference, for instance in the sigmoid notch of the wrist.

The invention is not restricted to this application and can be used when treating bones of the elbow, knee, and ankle. These applications may require a change in the shape of the inventive device related to each specific application, but the same principles are used irrespective of the site of the misalignment. However, the major use of the invention is expected to be for treating deformities and disorders of the distal radial ulnar joint.

The treatment of joint misalignment has been a problem because of the frequency of the injury disorders and the difficulties in correct treating.

The object of the invention is to restore an alignment between the radius and the ulna in order to prevent arthritis and to relieve pain as well as to minimize the impaction and pressure between the ulna and the carpus of the wrist. Misalignment between the radius and the ulna can result from injury or idiopathic conditions where the ulna is excessively long in relationship to the radius. Injuries that result in a fracture or dislocation of the radius can end up producing a radius that is too short in relationship to the ulna that allows the prominent distal end of the ulna to impact and apply excessive pressure to the carpus of the wrist, the triangular fibre cartilage that covers the distal end of the ulna.

There are essentially five general groups of options available for treatment of misalignment between the radius and the ulna or the joint referred to as the distal radius ulnar joint, these are:

(1) Complete excision of the distal end of the ulna,
(2) Partial excision of the distal end of the ulna,
(3) Excision of the ulna and replacement with a prosthetic joint,
(4) Fusion between the radius and the ulna with excision of a segment proximal to the fused joint to create a false joint, and
(5) Shortening of the ulna.

Excision of the distal end of the ulna can relieve the pain resulting from arthritic joints or increased pressure and impaction between the ends of the ulna and the carpus, but it results in an unstable joint, which frequently increases instability of the ulna that produces additional symptoms for which no treatment options can subsequently restore the action of the destroyed joint.

Partial excision of the end of the ulna strives to relieve the pressure between the ulna and the carpus while still allowing some portion of the joint to reserve a normal relationship and rotation between the radius and the ulna. Unfortunately, many patients experience significant pain because the normal cartilage and joint contacting between the triangular cartilage and ulna have been removed.

Removal of the distal ulna and replacement with a prosthetic joint allows for correction of the length of the ulna at the time of joint replacement, and may be satisfactory in older patients, but in younger, active patients the action between the metal surface of the ulna will cause destruction of the normal cartilage of the radius, with which it articulates. The loss of cartilage from the radius can result in recurrence of pain in the patient.

Arthrodesis of the joint and the creation of a false joint proximalis by removing a segment of bone have been referred to as the Sauve-Kapandji procedure. Although this can relieve symptoms of pain because the joint is fused, the rate of arthrodesis is unreliable and the false joint below can cause instability, clicking, and pain that is very difficult to treat because the resected bone can cause instability and pain.

Shortening osteotomies have been developed to preserve the normal joint and restore the correct alignment between the radius and the ulna. However, a failure to properly coat the bone surfaces of the osteotomy can result in delayed healing or a non-union.

A few major techniques have been developed, which include both a transverse osteotomy, as well as an oblique osteotomy. A comparison study demonstrated that transverse osteotomies require 21 weeks to heal while the oblique osteotomies healed in 11 weeks. (Reference Rayhack J M, Gasser S I, Latti L L, Ouellette E A, and Maline E L: Precision oblique osteotomy for shortening of the ulna, JHS 1993, Vol. 18A: 908-18). Oblique osteotomies can be performed either with or without the use of a lag screw through the plate and across the osteotomy to improve the compression. Providing a lag screw across the osteotomy site substantially improves the compression of the site and enhances bone healing. It is difficult to compress the bones, as there are other tissues attached to the bone that prevent the compression.

Few major techniques for providing the bone compression involve making an unguided or free hand bone cut followed by the application of a plate. This requires multiple assistance to guide the bone ends together while the osteotomy is performed.

The other method is to use a cutting guide and then apply a device with a compression screw system to bring the bone ends together. The freehand technique has a high margin of error and if the bone surfaces are not cut parallel, there is poor coaptation of the bones and a high rate of non-union. Also, the amount of bone removed is very imprecise. The technique that uses a cutting guide with the compression screw requires that the cutting guide be removed before applying the final plate implant. This technique will result in loss of alignment once the cutting guide is removed, as the final implant in the bone being cut cannot be visualized, and if the cutting guide provides any errors because of the way the device is assembled, significant problems may occur. The cutting guide from this device blocks and prevents the surgeon or physician from viewing the structures around the bone and injury to the bony structures by the saw can occur. Finally, this device uses two separate screws for compression of the osteotomy that cannot be compressed at the same time. As a result, misalignment between the bone surfaces often occurs.

Contrary hereto, according to the invention, a method of oblique osteotomy for the bone shortening is described, which allows for lag screw compression through the plate and can be performed while the plate is already attached to the bone, thus preventing loss of alignment.

The osteotomy can be directly visualized while the plate is in place in order to make sure that the physician can ensure that the cuts are accurate and that all soft tissues around the bone can be protected. A single central screw compression is all that is needed between the bone ends created to optimise the healing of the osteotomy.

SUMMARY OF THE INVENTION

The object of the invention is to provide implantable means for bone shortening to restore joint alignment, which overcomes the problems associated with the known art.

The means according to the invention has three functions, (1) bone shortening with an oblique osteotomy, (2) compression screw fixation across the osteotomy, and (3) stabilization with a plate implant that is applied to the bone prior to making the osteotomy. The plate implant is applied to the bone with an excavated or recessed portion of the plate centered over the site where the osteotomy is desired. The plate is compressed to the bone. Pressure is applied to the plate using one or more screws in the distal three holes of the plate. Fixation guides are arranged on the side of the plate and the surgeon selects the width of the bone to be removed based on a cutting guide to be applied in said fixation guides.

Two, three, or arbitrarily millimetres thick bone wafers can be removed with the guides that will be available. The surgeon can protect the soft tissues with retractors on either side of the bone and directly visualize while the cuts are completed. At one to two centimetres proximal to the proximal end of the plate a screw is inserted through one cortex—a 3.5-millimeter screw is inserted through one cortex of the bone to be used as a post for compressing the osteotomy.

Once the bone wafer has been removed, a compression screw device is attached to the plate with the aim of bringing the bone ends thus created together for achieving perfect conditions for coaptation of the leg or bone.

A unique feature of the plate is that it functions both as a drill guide, incorporated in the plate, as well as providing the guide for the osteotomy and device for compressing the bone surfaces.

DESCRIPTION OF DRAWINGS

In the following the invention will be described more in detail, and reference is being made to the drawings illustrating one and further preferred embodiments thereof, in which.

DETAILED DESCRIPTION OF THE PREFERRED EMBODIMENTS

As can be seen from the set of drawings above briefly described, the preferred embodiment of a device, according to the invention, is here shown used in a treatment sequence (FIGS. 1 through 10) using a method according to the invention. The steps of said sequence will in the following be described with reference to all parts involved.

Figure 1A:
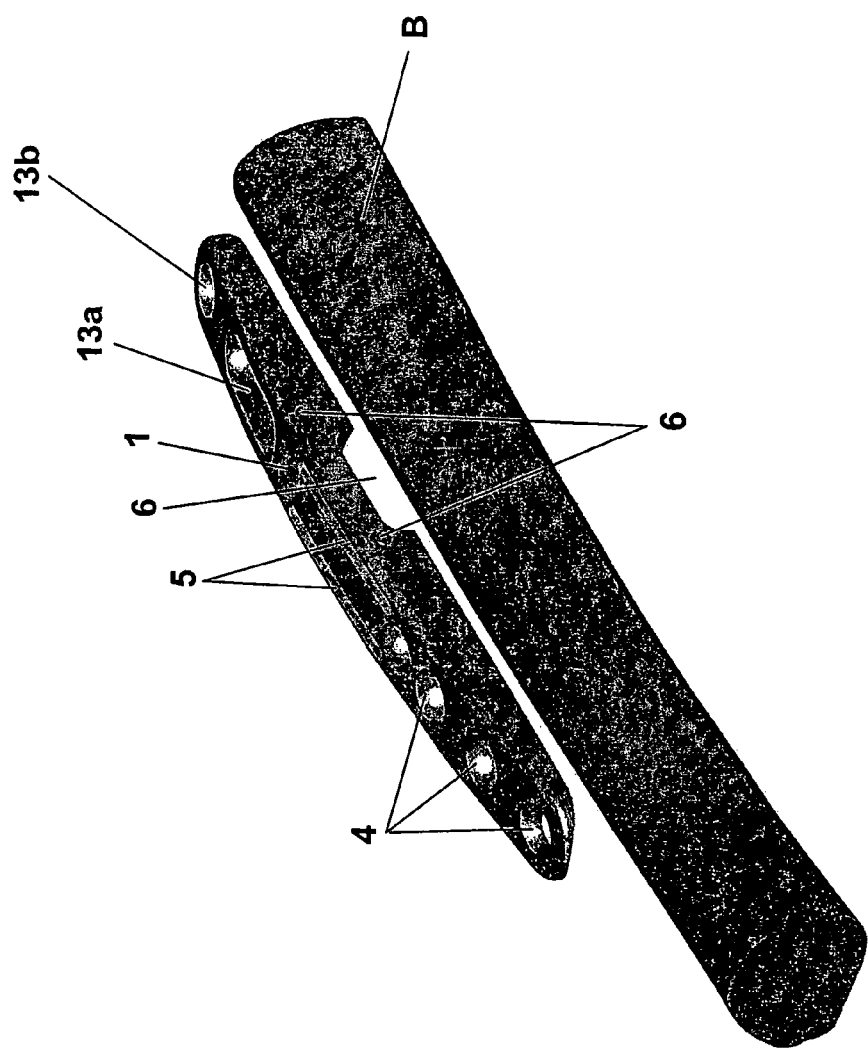
FIG. 1a shows in a perspective view on the one hand a part of a bone to be shortened and on the other hand a fixation device to be used for that purpose.

Thus, in FIG. 1a a section of a bone B is shown, which due to for instance a misalignment problem (as discussed above), is prone to be shortened. In connection thereto a fixation device 1 is arranged, here arranged parallel to, above and adjacent to said bone section or portion B.

Figure 1B:
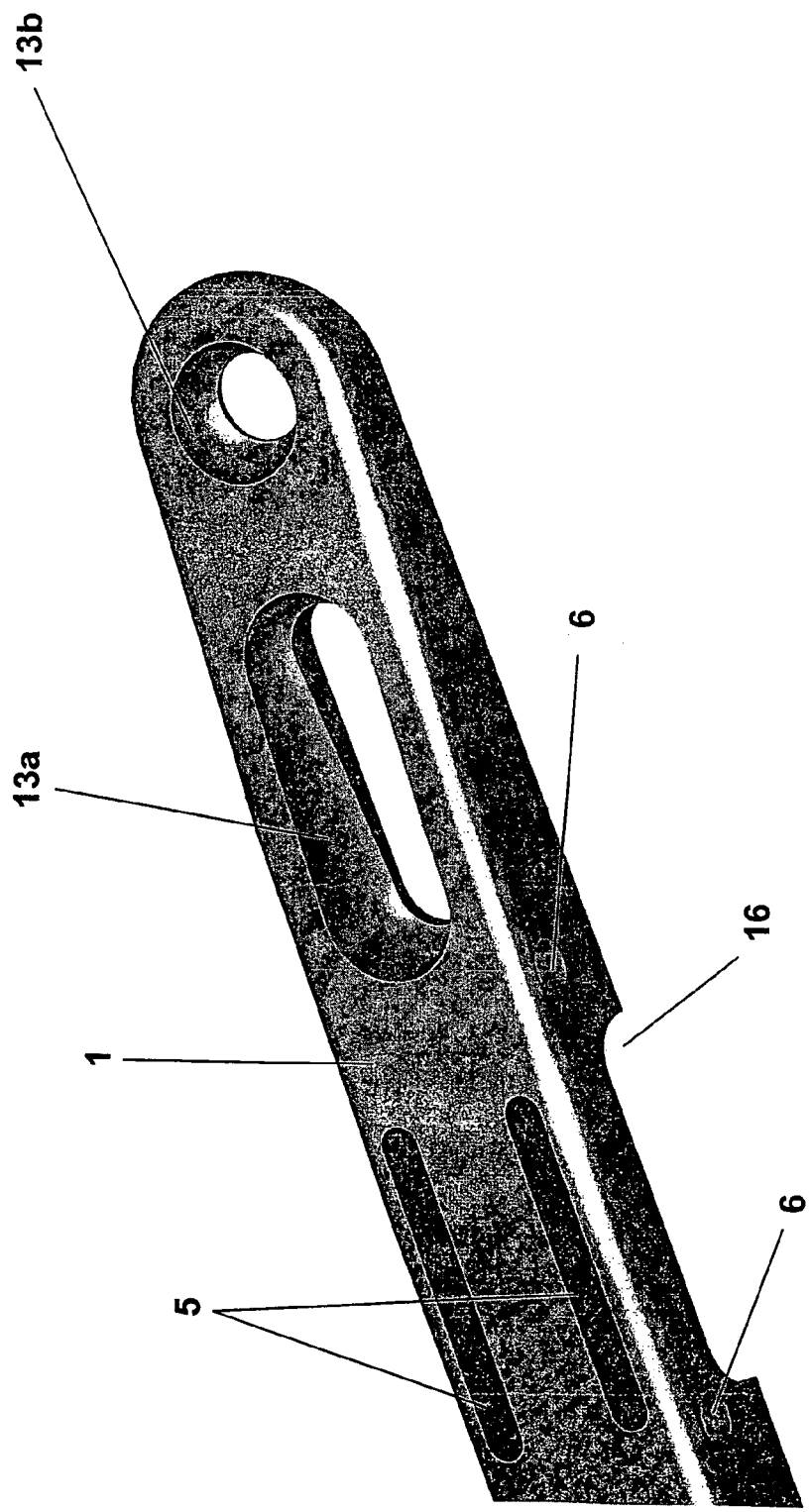
FIG. 1b shows in an enlarged partial perspective view an upper side of the fixation device exposing a design of apertures therein.
Figure 1C:
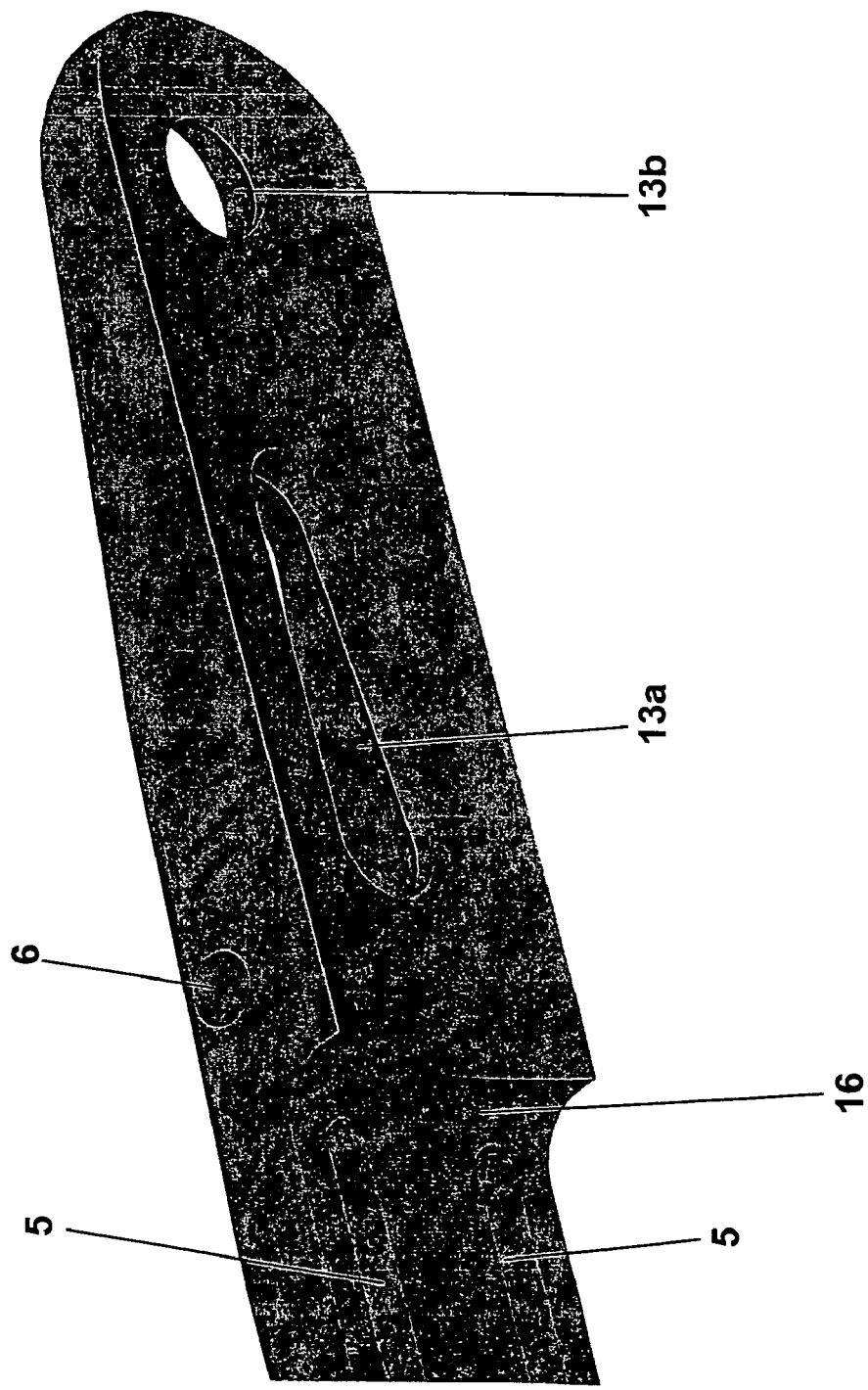
FIG. 1c shows likewise in an enlarged partial perspective view a bone-side of the fixation device and the design of said apertures as seen from this side.

In order to provide an enabling disclosure, FIGS. 1b and 1c show a specific part having cavities 13a and 13b. Important to note, is the countersink made in the cavity 13a, being provided with a slight slant to provide for a relatively easily handled screw joint, which is important for practical reasons after having performed a saw cut (see below).

Figure 2:
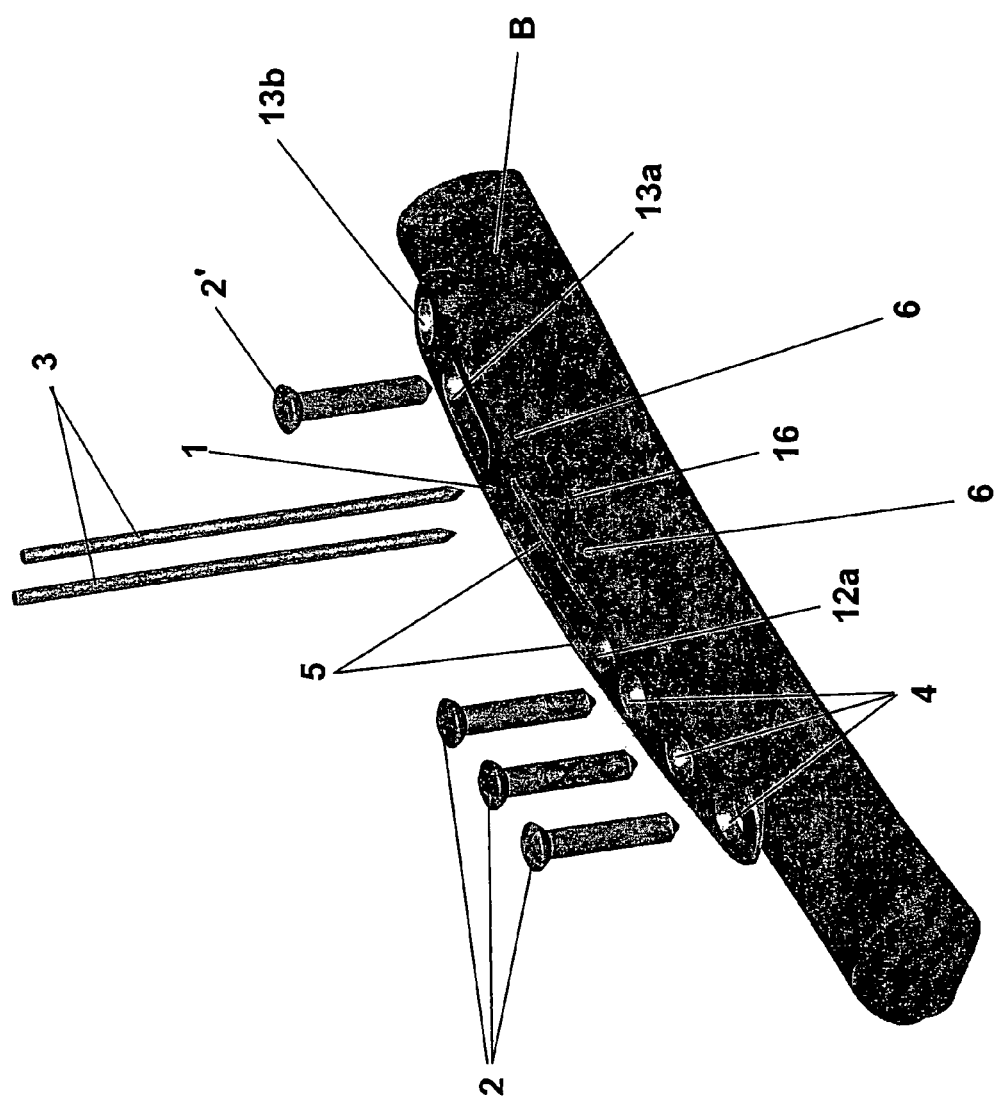
FIG. 2 shows in a perspective view a part of a bone where the fixation device together with screws and nails has been narrowed to the bone, FIG. 3, like in FIG. 2, shows a bone part together with the fixation device, where nails have been forced to penetrate cortex of the bone, three screws in FIG. 2, shown close to one another, have been tightly fastened and a screw, shown single in FIG. 2, has been fastened as well, while a cutting guide is shown in the vicinity of the fixation piece or device and the bone.

Furthermore, FIG. 2 shows that the fixation device 1 has been brought into close contact with a surface of the bone portion B. For illustrative purposes, four screws 2, 2' are used, on the one hand in a set of three screws 2, and on the other hand in a set of one separated screw 2' and two nails 3, each nail 3 shown in the vicinity of its related cavity 5.

Cavities or holes 4 are arranged and adapted for the first set of three nails 2 and a cavity or a slot 13a is adapted for said separated nail 2'. Between these sets 2; 3, 2' are said cavities 5 and adjacent said slot 13a is a further hole or slot 13b.

The two nails 3 are as shown aimed to be arranged in said cavities 5, which probably best can be described as elongated slots in said fixation device 1, the purpose of which will be described more in detail below. Also the cavity 13a for the separated screw 2' is, as previously mentioned, designed in an elongated fashion.

Figure 3:
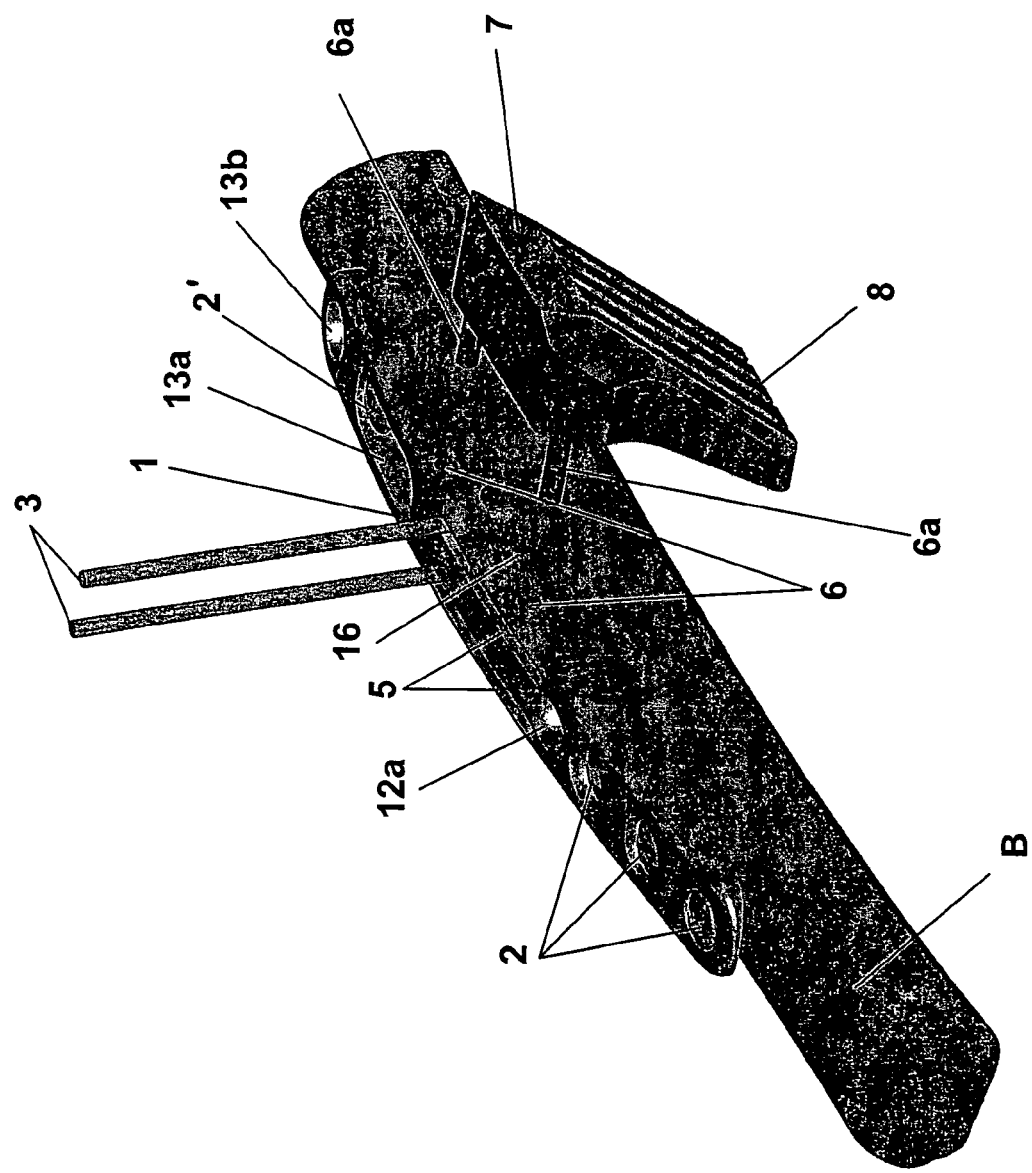

As is illustrated in FIG. 3 each of the three screws 2, and the separated screw 2' shown in FIG. 2, have been finally tightened and fixed as well as each of the nails 3 have been driven into a position in which they are tightly fixed to cortex of the bone B.

As can be seen from all FIGS. 1a through 3, said fixation device 1 includes two holes 6, which are arranged transversely to each axis of the holes or cavities 4, 5 and 13a of said device. The holes 6 are aimed for a temporary coaction with an arrangement formed as a cutting guide 7, which, here shown at a distance from the fixation device 1, is provided with guiding slots 8 for a saw blade.

Figure 4:
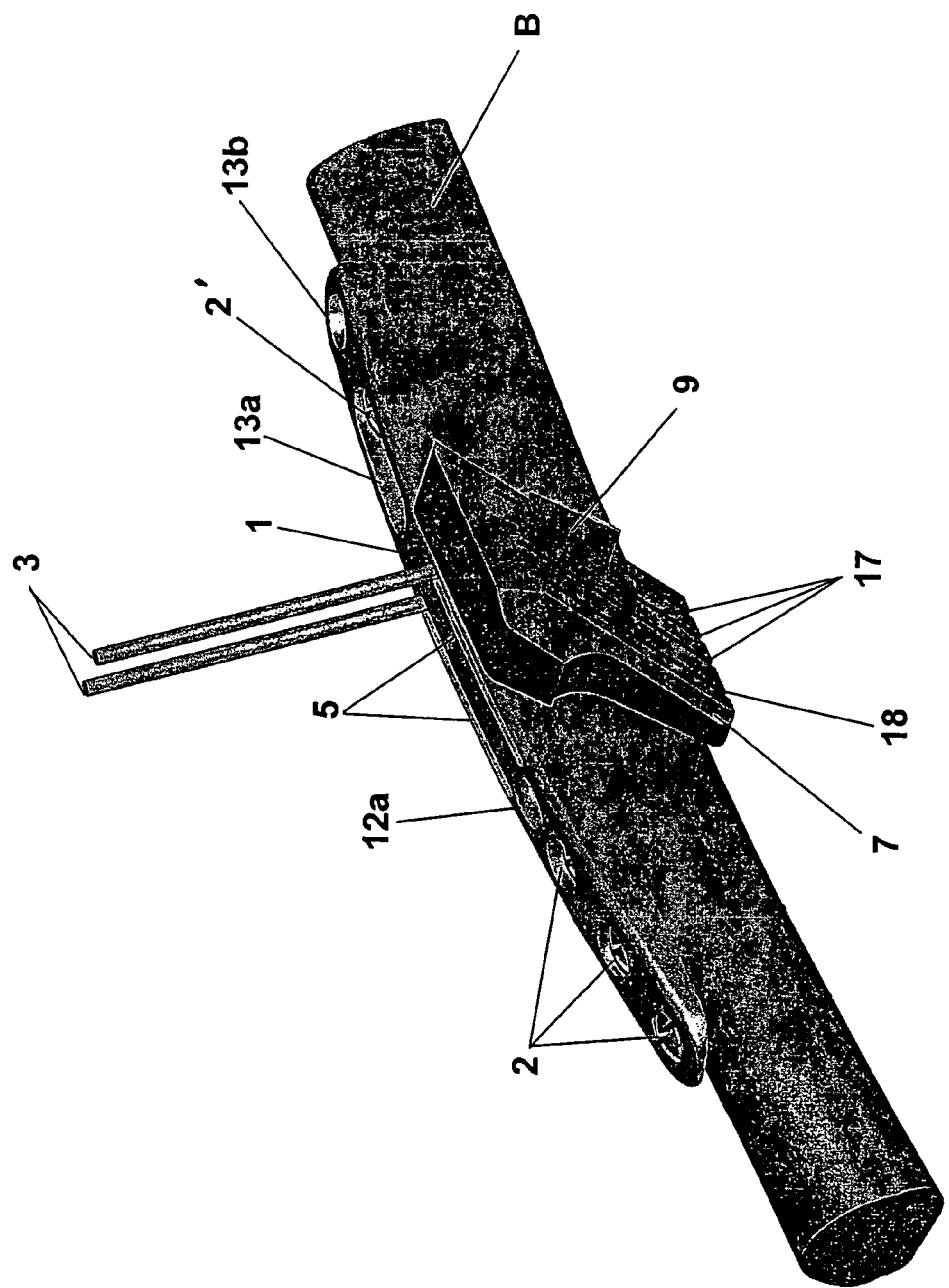
FIG. 4 shows the cutting guide in a position fixed to holes in the fixation device, close or adjacent to the bone, while a saw blade is being used to cut the bone.

FIG. 4 shows the fixation device 1 and the cutting guide 7 in coaction together with a saw blade 9, for excising an excessive part of the bone section or portion B shown.

Figure 5:
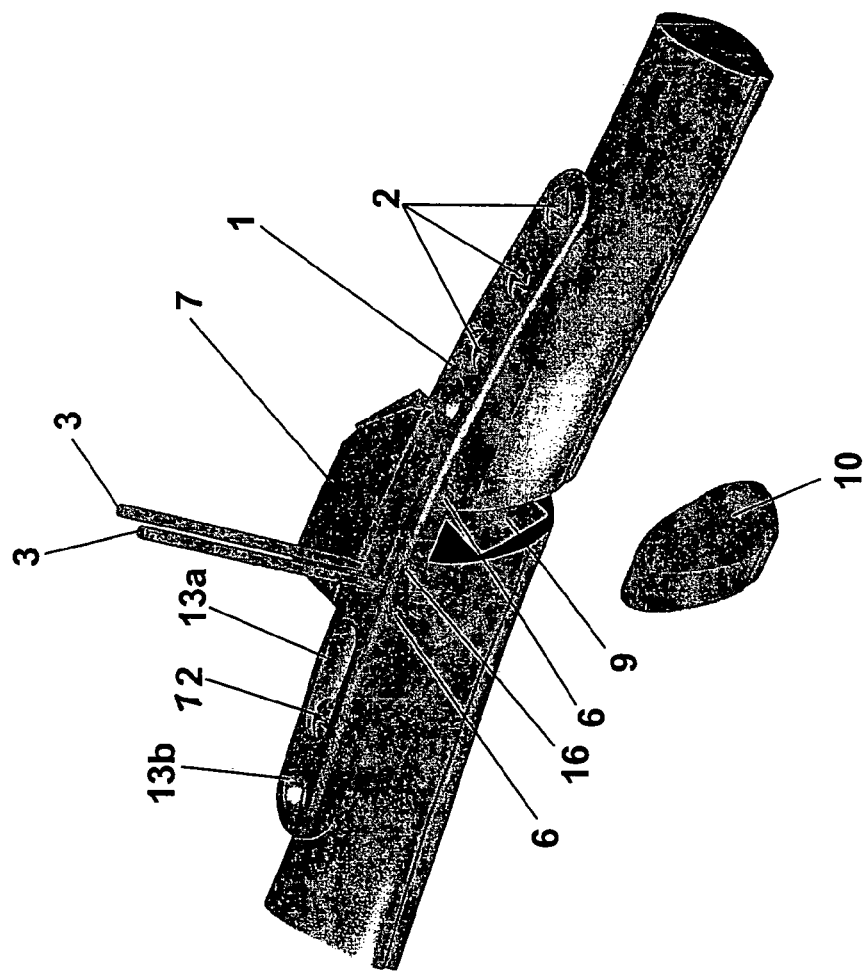
FIG. 5 shows the excision on a bone segment after the application and use of the saw blade, shown in FIG. 4, guided by slots in the cutting guide.

As seen from an opposite side of the cutting guide 7, arranged as illustrated in FIG. 4, FIG. 5 shows the excision operation completed with an excised bone portion 10 as a separated part and with the saw blade 9 in its final position.

Figure 6:
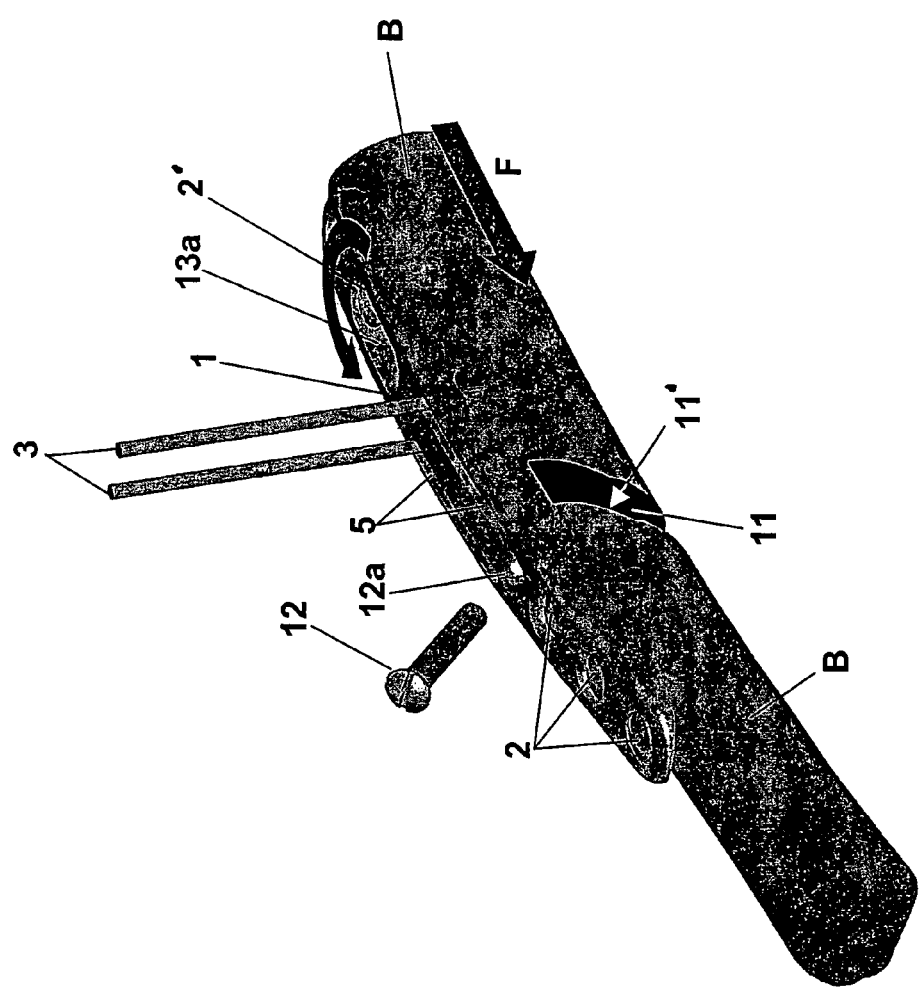
FIG. 6 shows how the bone ends, after removal of the cutting guide, are to be brought together, which is allowed by slightly releasing the screw arranged single and letting the nails slide along the slots of the fixation device, as they are arranged during application of a force "F" to bring the bone ends together.

FIG. 6 in turn shows how, after excision of the excessive bone portion 10, both bone end surfaces 11 and 11' thus created are pushed together by applying a force F, however this may be done only after a temporarily release of the screw 2' (illustrated by an arrow) in its elongated and slantedly designed hole 13a.

Thereafter, the bone end surfaces 11 and 11' are to be fixed in relation to each other and this is done by using an additional screw 12, which is obliquely arranged in relation to a main direction of the bone, however transversely arranged to each of the bone end surfaces 11 and 11' thus created.

According to FIGS. 7a through 7f three different alternatives are illustrated in order to exemplify how to bring the bone ends 11 and 11' together.

In all three alternatives one leg 20 in the pair of pliers P is attached to one of the holes 6 for the cutting guide 7 discussed above.

More precisely one leg is arranged in the one of the holes 6 situated most close to a cavity or a hole 12a for the screw 12 to be obliquely arranged relative to said axis of the bone B.

The other leg 21a of said pair of pliers is in each of the alternatives illustrated applied differently.

Figure 7A:
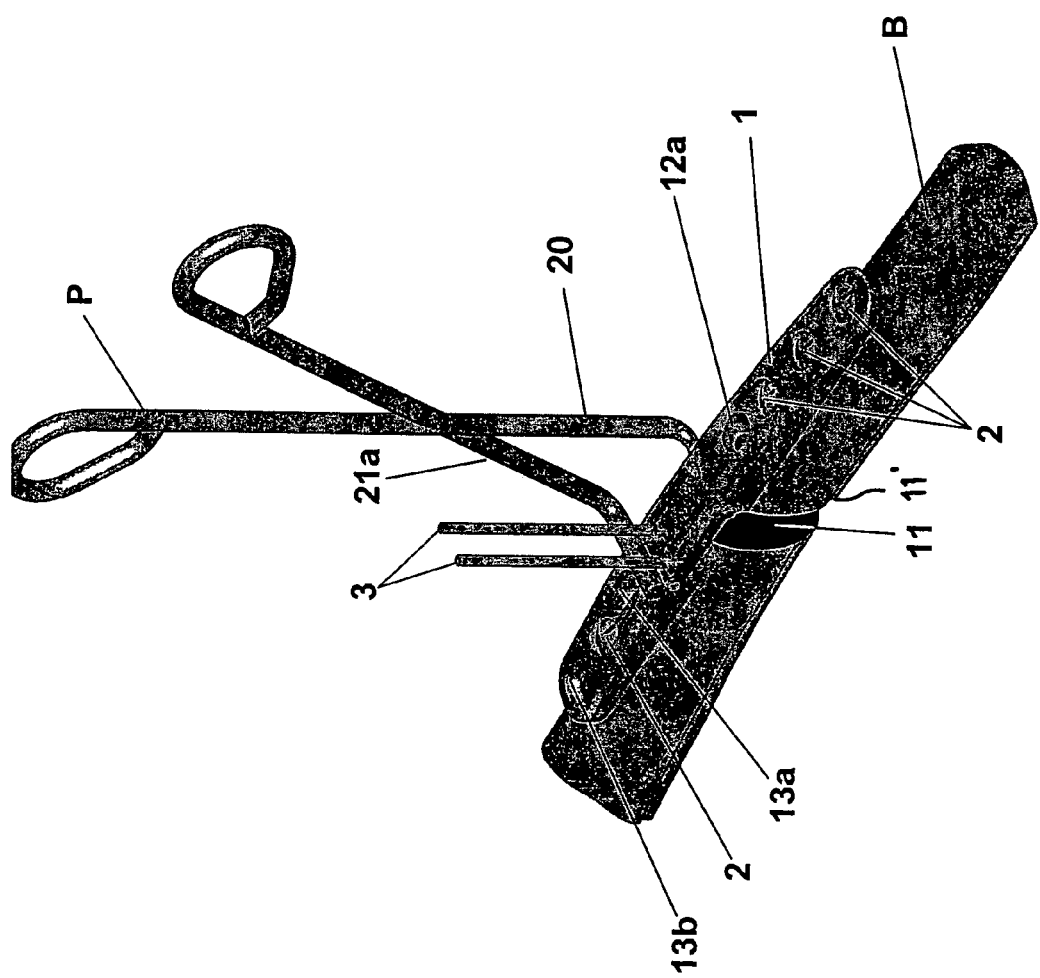
FIGS. 7a and 7b show the use of a pair of pointed pliers and how, by applying the force "F", the bone ends can be brought together, according to a first alternative, FIGS. 7c and 7d likewise show the use of a said pair of pliers, however arranged differently, for applying said force "F", according to a second alternative, FIGS. 7e and 7f likewise show, however in accordance with a third alternative, a preferred use of said pair of pliers for applying said force "F"
Figure 7B:
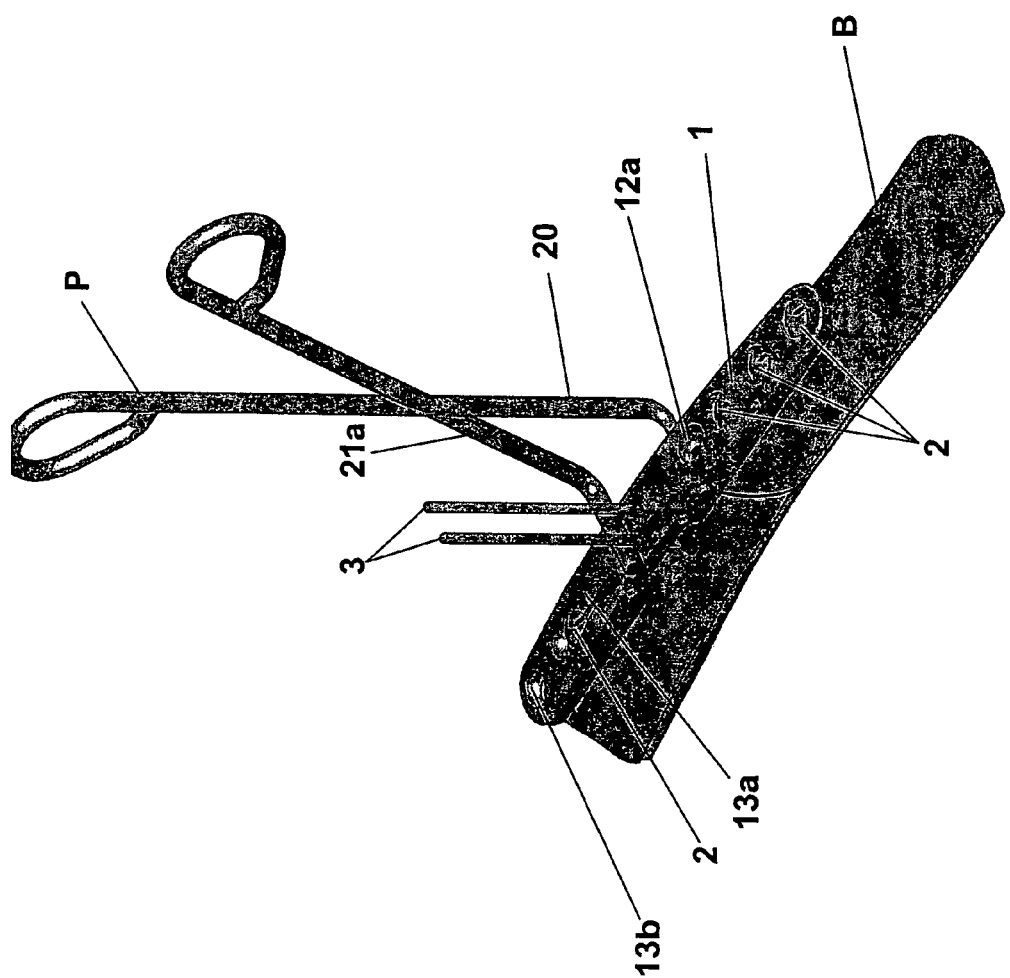
Figure 7C:
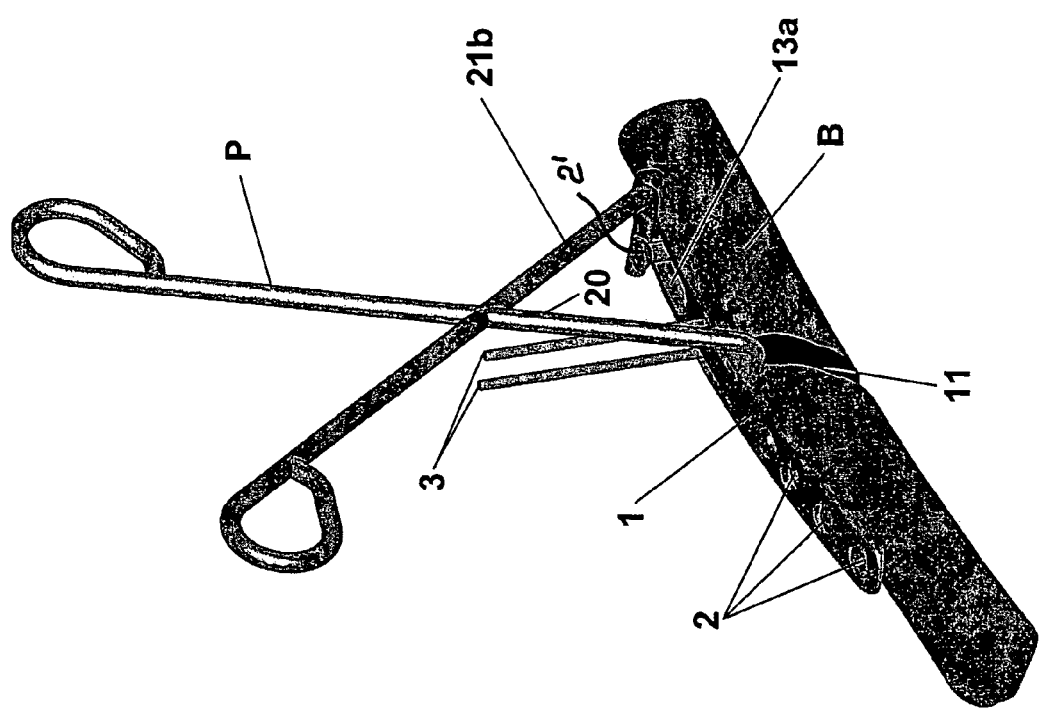
Figure 7D:
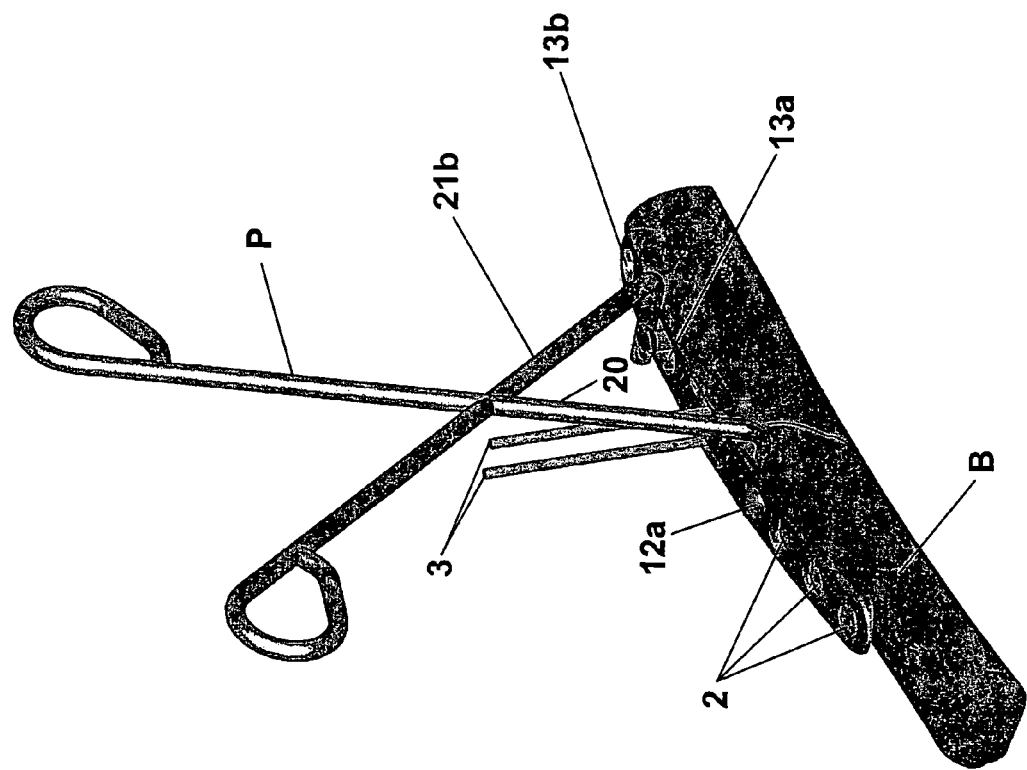

According to FIGS. 7a and 7b the leg 21a is applied behind the two nails 3 to enable the bone end surfaces 11 and 11' to be forced together, while according to FIGS. 7c and 7d said leg 21b is hooked around the screw 2', arranged in the cavity 13a after the same has been suitably loosened as shown.

Figure 7E:
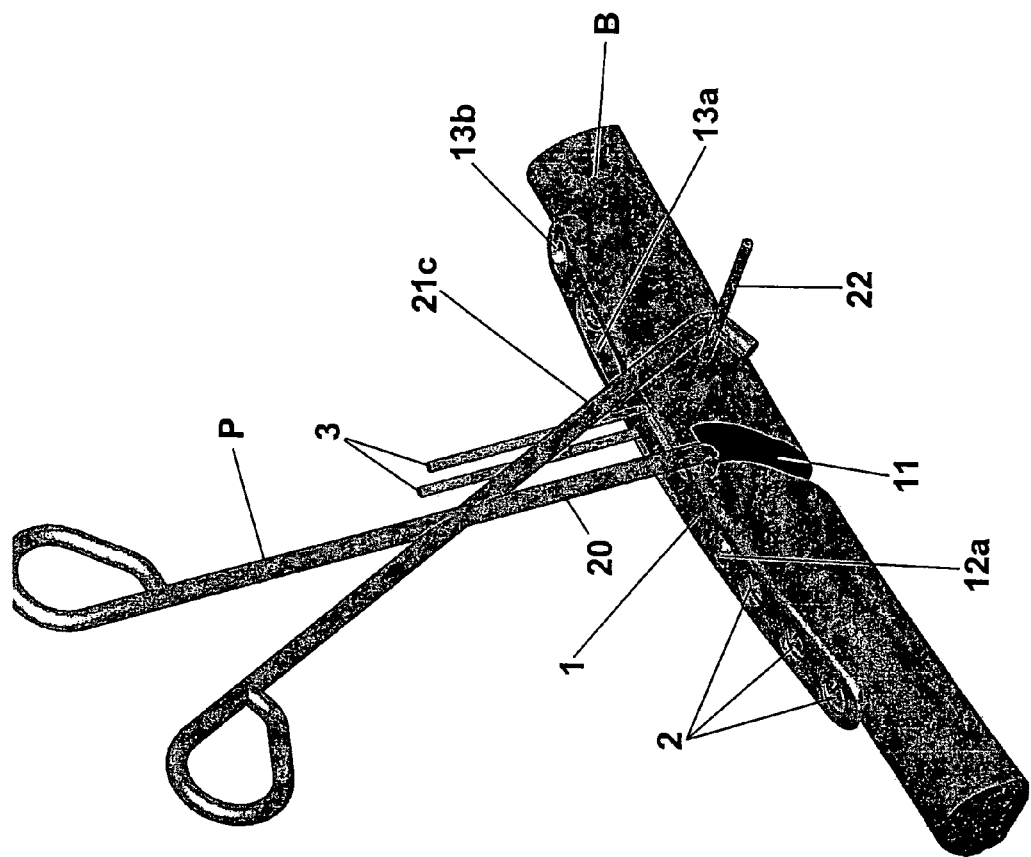
Figure 7F:
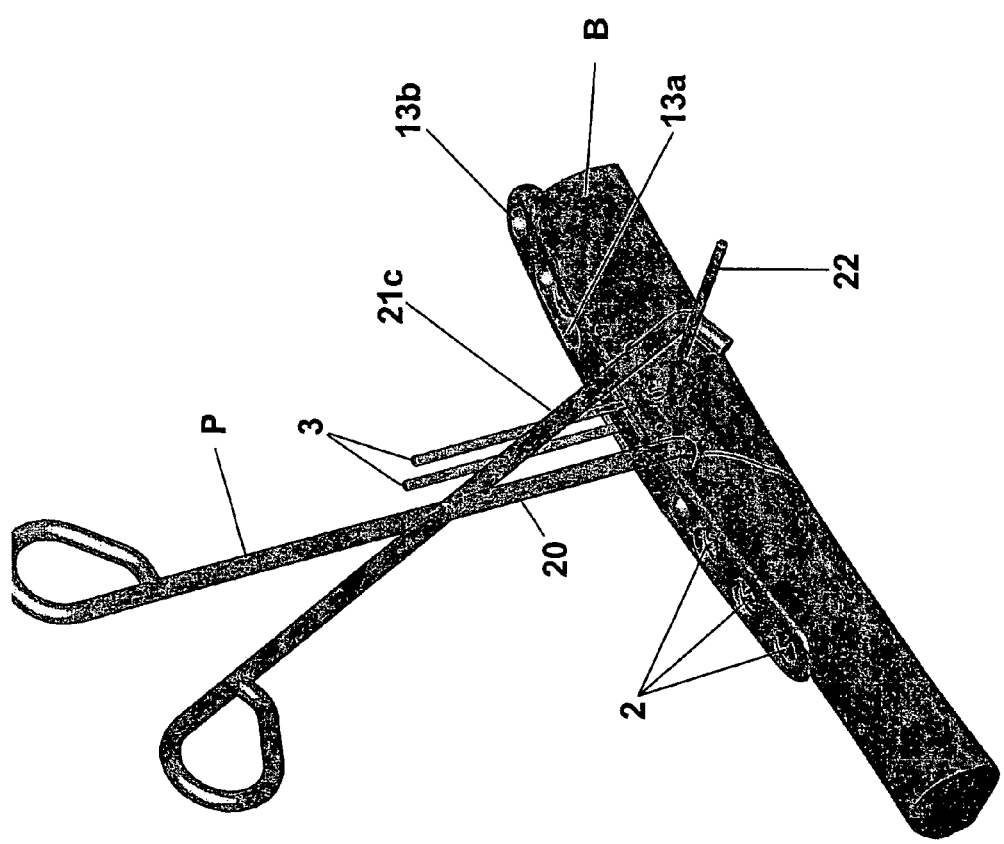

Last but not least according to FIGS. 7e and 7f, said leg 21c of the pair of pliers is hooked around an additional nail 22, fixed to the side of the bone cortex for this purpose only.

As is conventional, in all three of said alternatives, the pliers and associated legs are used in a manner so as to press the bone ends 11 and 11' together. After so doing, the pressure of the pliers is upheld while the separated screw 2' in the cavity 13a is tightened. The specific design of the elongated cavity 13a then makes the achieved position for the slided bone ends 11 and 11' automatically to lock itself in that position.

Figure 8:
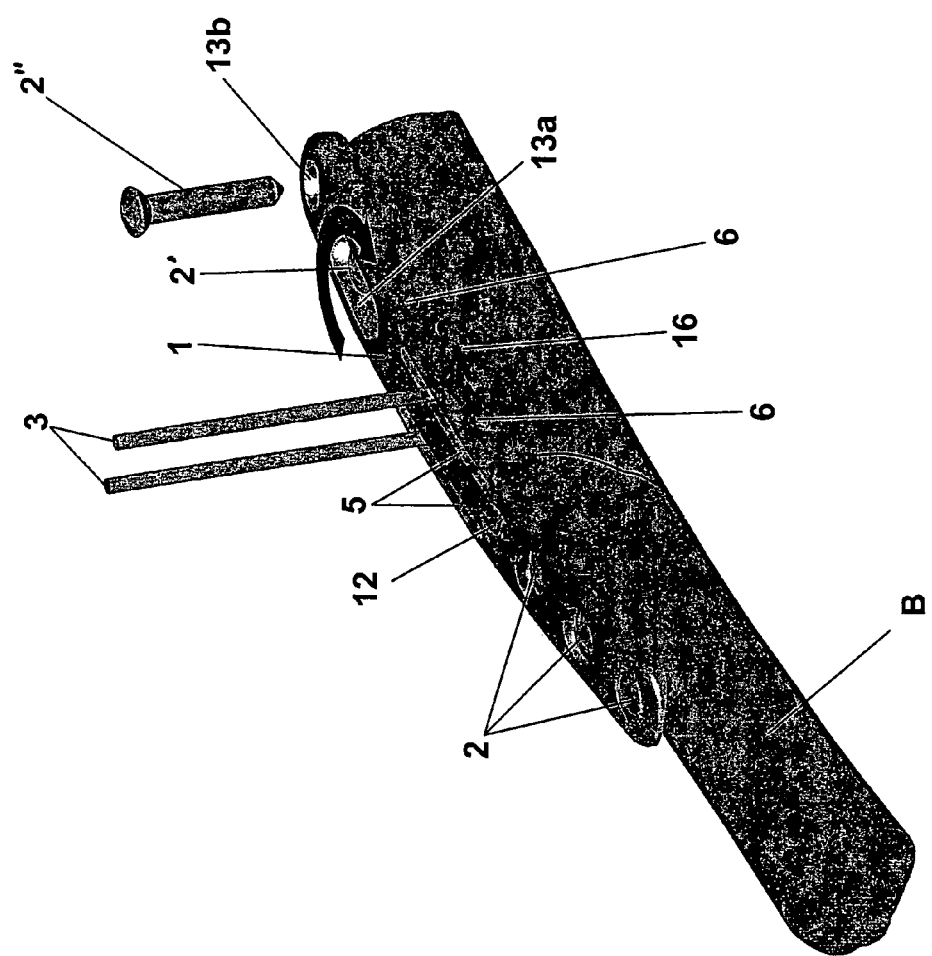
FIG. 8 shows, after bringing the bone ends together and fixing them with an oblique screw joint, that said singly arranged screw is re-tightened and another screw, beyond the same, is screwed into the same bone end.

Thus the bone end surfaces 11 and 11' have been brought together and are thereafter, as can be seen in FIG. 8, fixed to each other by using the screw 12, however, first after tightening the screw 2' in the cavity 13a. Please specifically note the distance "travelled" by the two nails 3 in their elongated holes or slots 5. Said distance is for reasons that are easily realised more or less equivalent to the length of the excised bone portion 10.

FIG. 8 shows the finally united bone end surfaces 11 and 11', between which the osteotomy has been performed, and how the bone end surfaces 11 and 11' just have been secured together by making use of said screw 12 as well as of retightening the screw 2' in the hole or cavity 13a.

Another screw 2", shown apart from the bone portion B and the fixation device 1, is to be arranged in a hole 13b, arranged further away from the hole or slot-formed cavity 13a.

Figure 9:
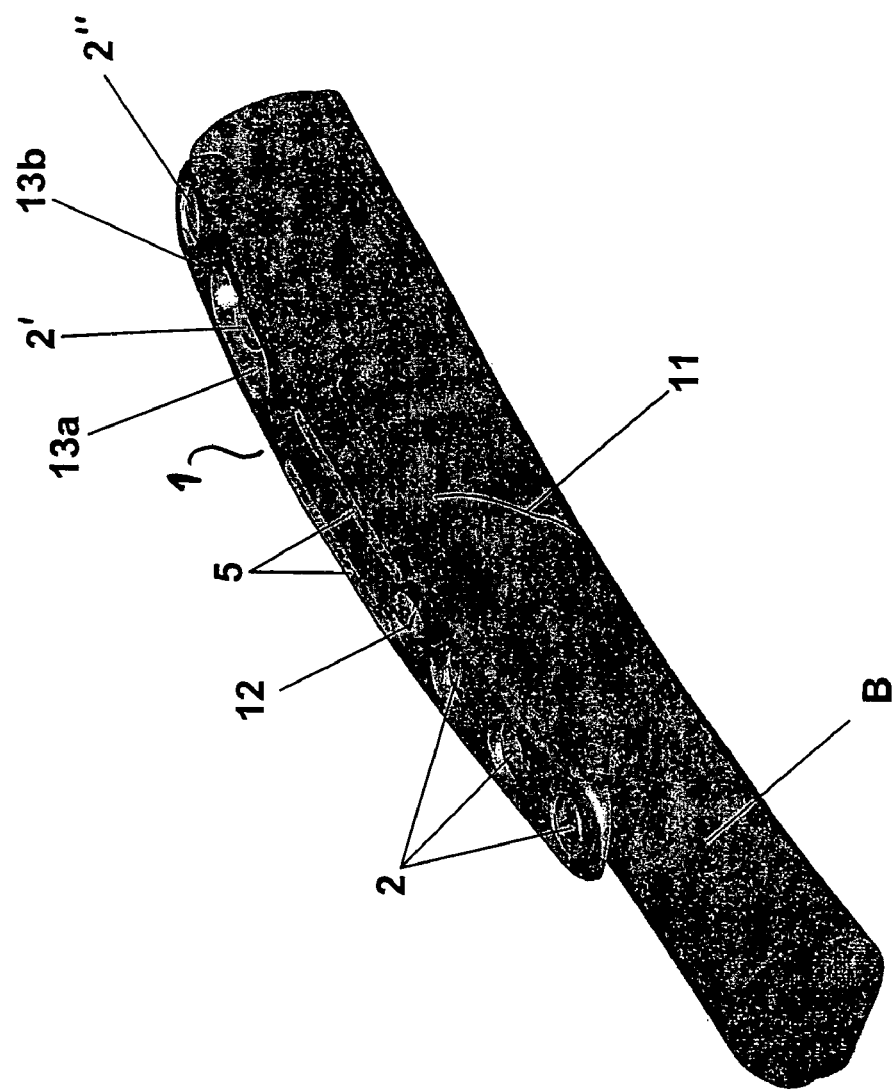
FIG. 9 shows a situation after a removal of the nails, and FIG. 10 finally shows how, if preferred, an extra screw may be inserted through the slot where previously said single screw was slideably arranged.
Figure 10:
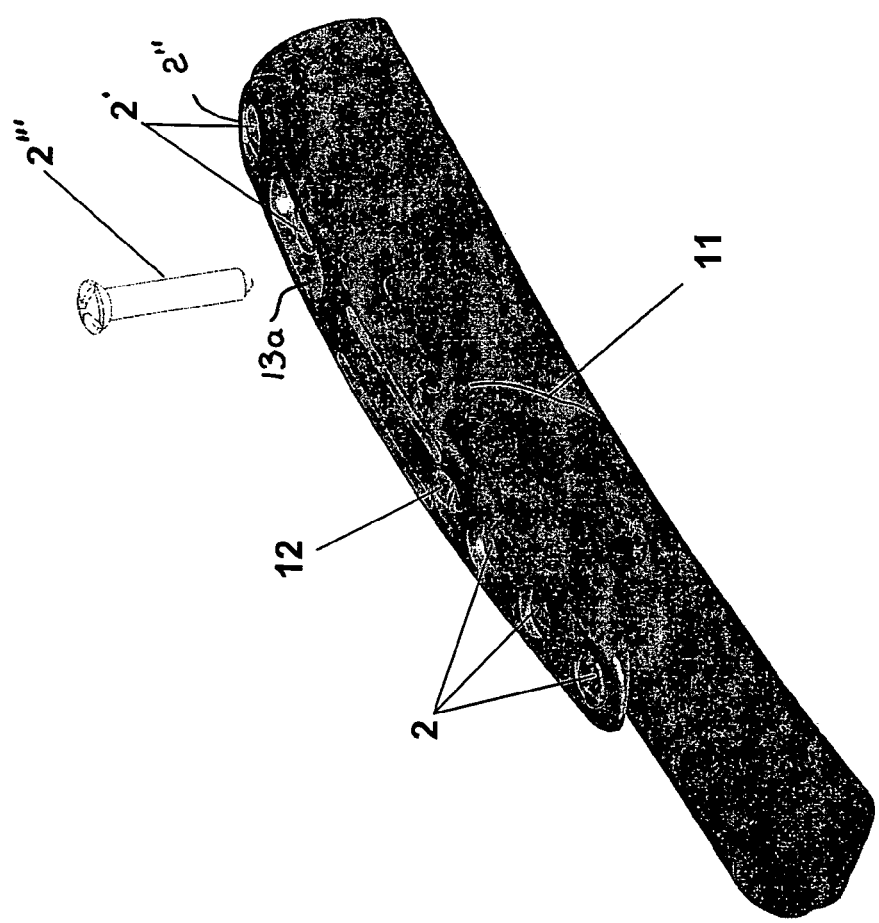

FIG. 9 shows the bone portion B and the device 1 in their final relative positions except for the alternative shown in FIG. 10, where a further screw 2''' is arranged in an opposite end of the elongated slot or hole 13a.

As is disclosed on all illustrations, except FIG. 4, the fixation device 1 includes a recess 16, which is supposed to be placed facing the part of the bone to be excised during the osteotomy operation. The purpose of the recess 16 is on the one hand to provide a space in connection to the healing zone, not to cause interference where not needed between natural tissue such as the bone and the fixation device, and on the other hand to make sure that later on, when looking at the healing zone with the aid of X-ray methods, provide for best possible visibility of the healing-zone.

The method according to the invention will hereinafter be described in a consecutive manner. As is completely clear and easily understandable, all necessary and usual preparations normally made in these circumstances also have to be performed when making an osteotomy using the method and device according to the present invention.

Having performed all such necessary measures, the bone on which the osteotomy is to be performed lies relatively open and free to the surgeon.

Initially, thus the device 1, according to the invention, is applied to the surface of the bone portion B just above the area where the excision is to be made. Holes in a dimension suitable for the screws 2 to be used are drilled, using the holes 4 as a template, whereupon said device 1 is fixed to the bone surface by said set of three screws 2.

In using the device 1 as a template for drilling purposes it may prove useful to apply a clamp (not shown) around the bone B and the device 1, in order to initially be able to properly fix the device 1 in relation to the bone B.

At an end portion of the elongated hole 13a, facing towards the just fixed three screws 2, another hole is drilled in the bone B and yet another screw 2' is fixed. Now the device 1 is properly fixed to the surface of the bone portion B and it is extremely essential that the screws are fixed properly in the three holes 4 and the hole 13a before the nails 3 are driven into the bone cortex. Consequently nails 3 are now driven into the bone cortex at the ends of the elongated slots 5 situated most close to the cavity or hole 13a.

As can be seen from all the Figures, except FIG. 4, the holes 6 are arranged mainly for one purpose only, namely for the attachment of the cutting guide 7. Especially FIGS. 3 and 4 show how this attachment is preferred and how the saw blade 9 is applied.

At reference numeral 17 in FIG. 4 is shown a number of alternative slots 8 adapted to indicate where to place a first cut, and at reference numeral 18 is also shown a slot where to always make the last cut in order to excise a suitable bone portion 10.

After having performed two full through-cuts with the saw blade 9, the excessive bone part 10 is removed and as is shown in FIG. 6, after slightly releasing the screw 2' in the cavity 13a, the bone end surfaces 11 and 11' thus created are forced together by applying said force F as is shown in FIGS. 6 and 7*a* through 7*f*. By so doing the thus temporarily loosened bone portion, according to FIGS. 7*a* through 7*f*, is forced into contact with its counterpart with fully coinciding bone end surfaces 11 and 11'.

The movement of the temporarily slightly released bone portion is controlled rotationally by the nails 3, which are not to be removed until the device 1 later on is finally fixed in situ, and in relation to the device 1 via the screw 2' in the hole 13*a*.

After establishing such a bone end contact, a hole of a dimension suitable for fixing the screw 12 therein is drilled with the cavity or hole 12*a* as a template. The screw 12 is thereafter fitted to keep the bone ends 11 and 11' together. As seen in FIG. 8 the screw 2' in the cavity 13*a* is retightened and another screw 2" is in a fashion as described above fitted to a drilled hole, using the cavity 13*b* as a template.

Finally as shown in FIG. 9 a screw 2" is fitted to a hole drilled through the cavity 13*b* at the distal end of the device 1.

As an option an extra screw 2'" may be attached to the elongated cavity 13*a* in order to achieve an enhanced compression of the osteotomy.

The invention claimed is:

1. A method for cutting a bone and securing portions of the cut bone together the method comprising the steps of:
    positioning a longitudinally shaped fixation device to said bone where an excision is to be performed, said device having a first end and a second end;
    securing said device to said bone by using at least one fastener inserted through a hole defined by said first end of said device;
    securing said second end of said device to said bone by using at least one fastener inserted through at least one elongated hole defined by said second end of said device;
    securing a cutting guide temporarily to said fixation device by securing prefabricated guiding pins in guiding holes defined by said fixation device to enable a controlled cutting of a part or section of the bone;
    cutting said bone into at least two portions using a saw, wherein said cutting of said bone is performed by inserting the saw in slots arranged at fixed distances on the cutting guide to provide an exact measure of the amount to be cut and excised from the bone, whereby a perfect match between remaining bone ends of the at least two portions is achieved;
    moving said portions of said bone towards and into contact with each other while the device is still seared to the bone,
    wherein said fastener is movable together with its related bone portion relative to the elongated hole; then
    securing at least one fastener in a prefabricated elongated hole defined by the fixation device to transversely penetrate and secure said portions of said bone together, keeping a steady state, during which at least one fastener is used to secure the second end of the device to the bone such as to finally keep the bone ends together in order to heal.

2. The method of claim 1, wherein during initial steps of the osteotomy, three screws are inserted substantially transversely through said first end of the device and into the bone cortex, whereafter two nails and one screw are each arranged at the end of said elongated hole, whereby said latter screw aims to keep said second end of the device in close contact with the bone surface.

3. The method of claim 1, which includes using a pair of pliers having a first end and a second end to bring the portions of said bone together by inserting said first end of said pliers in a guiding hole defined by the first end of the fixation device and said second end of said pliers adjacent to a suitable head of a nail or a screw secured to an end of the bone which after the excision of a part thereof is located most distal to the first end of the fixation device.

4. A device for performing a surgical osteotomy, comprising;
    a body including an elongated portion made of a material dimensionally stabile at about 67° F. (37° C.), said body including a width of ⅔ to ⅘ of the diameter of the bone and a slightly curved planar surface, said body being placed against the surface of a bone,
    said curved planar surface having a mid portion defining an elongated recess substantially centered above a zone defined as a healing zone where the ends of portions of a cut bone are growing together,
    a first end of said body defining at least one hole for receiving a screw;
    a second end of said body defining at least one elongated aperture to be penetrated by one or more screws or nails to secure the device to the bone, said first end defining an additional hole (perpendicular to a sawing plane) for a screw to keep both bone ends together after excision; and
    a cutting guide including two guiding pins that are inserted into two corresponding securing holes defined by said body to temporarily secure said cutting guide to said body, said cutting guide defining at least two slots that are positioned adjacent to the bone to enable a saw to be inserted into the slots to provide for accurate sawing of the bone into at least two portions in a pre-chosen fashion,
    said body defining at least one hole configured to receive an end of a pair of pliers to facilitate the joining of the ends of the portions of the bone after the bone is cut and while the device is secured to the bone.

5. The device of claim 4, wherein the at least two slots are parallel to each other.

6. The device of claim 4, wherein the cutting guide defines a plurality of parallel slots arranged at predetermined distances from each other for ease of decision when planning a sawing operation.

* * * * *

UNITED STATES PATENT AND TRADEMARK OFFICE
CERTIFICATE OF CORRECTION

| | | |
|---|---|---|
| PATENT NO. | : 7,540,874 B2 | |
| APPLICATION NO. | : 10/854892 | |
| DATED | : June 2, 2009 | |
| INVENTOR(S) | : Thomas E. Trumble and Lars Tellman | |

It is certified that error appears in the above-identified patent and that said Letters Patent is hereby corrected as shown below:

Claim 1, col. 7, line 49, "seared" should read --secured--.

Signed and Sealed this

Eighth Day of September, 2009

David J. Kappos
*Director of the United States Patent and Trademark Office*